US007425558B2

(12) United States Patent
Sukoff Rizzo et al.

(10) Patent No.: US 7,425,558 B2
(45) Date of Patent: Sep. 16, 2008

(54) SEROTONERGIC AGENTS FOR TREATING SEXUAL DYSFUNCTION

(75) Inventors: Stacey J. Sukoff Rizzo, Levittown, PA (US); Sharon Joy Rosenzweig-Lipson, East Brunswick, NJ (US); Wayne Everett Childers, New Hope, PA (US); Michael Kelly, Thousand Oaks, CA (US); Lee Erwin Schechter, Toms River, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/506,514

(22) Filed: Aug. 18, 2006

(65) Prior Publication Data

US 2006/0287333 A1    Dec. 21, 2006

Related U.S. Application Data

(63) Continuation of application No. 11/396,307, filed on Mar. 30, 2006, which is a continuation-in-part of application No. 11/330,907, filed on Jan. 11, 2006, which is a continuation of application No. 10/441,536, filed on May 20, 2003, now Pat. No. 7,026,320, which is a continuation of application No. 10/218,251, filed on Aug. 14, 2002, now Pat. No. 6,586,436, which is a continuation of application No. 10/010,575, filed on Nov. 13, 2001, now Pat. No. 6,469,007.

(60) Provisional application No. 60/297,814, filed on Jun. 13, 2001, provisional application No. 60/253,301, filed on Nov. 28, 2000.

(51) Int. Cl.
   *A61K 31/496* (2006.01)
(52) U.S. Cl. .................................. 514/253.11; 544/364
(58) Field of Classification Search ............. 514/253.11
   See application file for complete search history.

(56) References Cited

U.S. PATENT DOCUMENTS

| 5,532,244 | A | 7/1996 | Wong et al. |
| 5,532,250 | A | 7/1996 | Wong et al. |
| 5,532,264 | A | 7/1996 | Wong et al. |
| 5,532,268 | A | 7/1996 | Wong et al. |
| 5,538,992 | A | 7/1996 | Wong et al. |
| 5,552,429 | A | 9/1996 | Wong et al. |
| 5,756,532 | A | 5/1998 | Stack et al. |
| 5,776,969 | A | 7/1998 | James |
| 6,127,357 | A | 10/2000 | Cliffe et al. |
| 6,169,105 | B1 | 1/2001 | Wong et al. |
| 6,566,112 | B2 | 5/2003 | Jones et al. |
| 7,026,320 | B2 | 4/2006 | Childers et al. |

FOREIGN PATENT DOCUMENTS

| EP | A-0512755 | 11/1992 |
| EP | 0 687 472 | 12/1995 |
| EP | 0 792 649 | 9/1997 |
| WO | WO-94/13643 | 6/1994 |
| WO | WO-94/13644 | 6/1994 |
| WO | WO-94/13661 | 6/1994 |
| WO | WO-94/13676 | 6/1994 |
| WO | WO-94/13677 | 6/1994 |
| WO | WO-95/33725 | 12/1995 |
| WO | WO-95/33743 | 12/1995 |
| WO | WO-97/03982 | 2/1997 |
| WO | WO-02/44142 | 6/2002 |
| WO | WO-2004/082686 | 9/2004 |

OTHER PUBLICATIONS

Beresford et al. Expert Opin.Emerging Drugs, vol. 8(1),p. 103-122 (2003).*
Wood et al. Expert Opin.Investig.Drugs, vol. 11(4), p. 457-467 (2002).*
Jankovic Mount Sinai Journal of Medicine, vol. 73, p. 682-689 (2006).*
Testa et al. BJU International, vol. 87, p. 256-264 (2001).*
Borg, Psychopharmacology, vol. 185, pp. 389-394 (2006).*
Volpicelli, Medications for Alcoholism Treatment, posted on the web on Mar. 21, 2002 at http://www.tgorski.com/Medication/medications_for_alcoholism_treatment.htm) , pp. 1-17.*
Blackburn, Drug Discovery Today:Therapeutic Strategies, vol. 1, p. 35-41 (2004).*
Jones, et al, Pharmacology Biochemistry and Behavior 71, p. 555-568 (2002).
Robichaud, et al., Annual Reports in Med. Chem., Nov. 20, 2000, 35.
Sukoff Rizzo, et al., Society for Neuroscience Abstract #559.4 (2005).
Van Steen, et al., J. Med. Chem. 37:2761-2773 (1994).
Alexandre et al., 2006, Early Life Blockage of 5-Hydroxytryptamine 1A Receptors Normalizes Sleep and Depression-Like Behavior in Adult Knock-Out Mice Lacking the Serotonin Transporter, J. of Neuroscience 26(20)5554-5564.
Artigas et al., 1996, Acceleration of the effect of selected antidepressant drugs in major depression by 5-HT1A antagonists, Trends Neurosci. 19(9):378-383.
Azmitia, 2001, Neuronal instability: implications for Rett's syndrome, Brain & Development 23:S1-S10.
Berends et al., 2005, A Review of the Neuroprotective Properties of the 5-HT $_{1A}$ Receptor Agonist Repinotan HCl (BAY x3702) in Ischemic Stroke, CNS Drug Reviews 11(4)379-402.
Blanchard et al., 1997, An Ethopharmacological Analysis of Selective Activation of 5-HT$_{1A}$ Receptors: The Mouse 5-HT$_{1A}$ Syndrome, Pharmacology Biochem. and Behavior 57(4) 897-908.
Boast et al., 1999, 5HT Antagonists Attenuate MK801-Impaired Radial Arm Maze Performance in Rats, Neurobiol. Learning Memory 71:259-271.
Cao et al., 1997, Influence of 5-HT$_{1A}$ Receptor Antagonism on Plus-Maze Behaviour in Mice, Pharmacology Biochem. and Behavior 58(2): 593-603.
Cao et al., 1998, Tolerance to acute anxiolysis but no withdrawal anxiogenesis in mice treated chronically with 5-HT$_{1A}$ receptor antagonist, WAY 100635, Neuroscience and Biobehavioral Reviews 23:247-257.

(Continued)

*Primary Examiner*—Emily Bernhardt
(74) *Attorney, Agent, or Firm*—Wilmer Cutler Pickering Hale and Dorr LLP

(57) ABSTRACT

Methods and compositions are provided for treating sexual dysfunction, e.g., sexual dysfunction associated with drug treatment, using 5-HT$_{1A}$ receptor antagonists.

1 Claim, 4 Drawing Sheets

OTHER PUBLICATIONS

Carli et al., 1995, (S)-WAY-100135, a 5-HT$_{1A}$ receptor antagonist, prevents the impairment of spatial learning caused by intrahippocampal scopolamine, Eur. J. Pharmacol. 283:133-139.

Carli et al., 1997, The 5-HT$_{1A}$ receptor agonist 8-OH-DPAT reduces rats' accuracy of attentional performance and enhances impulsive responding in a five-choise serial reaction time task: role of presynaptic 5-HT$_{1A}$ receptors, Brain Res. 774:167-174.

Carli et al., 1999, WAY 100635, a 5-HT$_{1A}$ receptor antagonist, prevents the impairment of spatial learning caused by intrahippocampal administration of scopolamine or 7-chloro-kynurenic acid, Neuropharmacol. 38:1165-1173.

Carli et al., 2000, WAY 100635, a 5-HT$_{1A}$ receptor antagonist, prevents the impairment of spatial learning caused by blockade of hippocampal NMDA receptors, Psychopharmacol. 149:259-268.

Cheeta et al., 2001, The dorsal raphe nucleus is a crucial structure mediating nicotine's anxiolytic effects and the development of tolerance and withdrawal responses, Psychopharmacology 155:78-85.

Collinson et al., 1997, On the elevated plus-maze the anxiolytic-like effects of the 5-HT(1A) agonist, 8-OH-DPAT, but not the anxiogenic-like effects of the 5-HT(1A) partial agonist, buspirone, are blocked by the 5-HT1A antagonist, WAY 100635, Psychopharmacology (Berl). 132(1):35-43.

Cryan et al., 1999, Comparative effects of serotonergic agonists with varying efficacy at the 5-HT$_{1A}$ receptor on core body temperature: modification by the selective 5-HT$_{1A}$ receptor antagonist WAY 100635, J. Psychopharmacol. 13:278-283.

Dijk et al., 1995, NMDA-induced glutamate and aspartate release from rat cortical pyramidal neurons; evidence for modulation by a 5-HT$_{1A}$ antagonist, British J. of Pharmacology 115(1169-1174).

Duxon et al., 2000, Latency to paroxetine-induced anxiolysis in the rat is reduced by co-administration of the 5-HT$_{1A}$ receptor antagonist WAY100635, British J. of Pharmaco. 130:1713-1719.

Fletcher et al., 1996, Electrophysiological, biochemical, neurohormonal and behavioural studies with WAY-100635, a potent, selective and silent 5-HT$_{1A}$ receptor antagonist, Behav. Brain Res. 73:337-353.

Gudelsky et al., 1986, Thermoregulatory responses to serotonin (5-HT) receptor stimulation in the rat, Neuropharmacology 25(12)1307-1313.

Harder et al., 2000, The 5-HT$_{1A}$ antagonist, WAY 100 635, alleviates cognitive impairments induced by dizocilpine (MK-801) in monkeys, Neuropharmacol. 39:547-552.

Hjorth et al., 1997, WAY 100653-induced Augmentation of the 5-HT-elevating Action of Citalopram: Relative Importance of the Dose of the 5-HT$_{1A}$Auto)receptor Blocker Versus that of the 5-HT Reuptake Inhibitor, Neuropharmacology 36(4/5):461-465.

Hughes et al., 1991, Symptoms of Tobacco Withdrawal, Arch. Gen. Psychiatry 48:52-59.

Hutson et al, 1988, Evidence that the hyperphagic response to 8-OH-DPAT is mediated by 5-HT$_{1A}$ receptors, Eur. J. of Pharmacology 150:361-366.

Joordens et al., 1998, The effects of 5-HT$_{1A}$ receptor agonists, 5-HT$_{1A}$ receptor antagonists and their interaction on the fear-potentiated startle response, Psychopharmacol. 139:383-390.

Jorgensen et al., 1999, Adrenocorticotropic Hormone Secretion in Rats Induced by Stimulation with Serotonergic Compounds, J. of Neuroendocrinology 11:283-290.

Kakizaki et al., 2001, Effects of WAY100635, a selective 5-HT$_{1A}$ receptor antagonist on the micturition-reflex pathway in the rat, Am. J. Physiol. Regul. Integr. Comp. Physiol. 280(5):R1407-1413.

Kalkman et al., 1995, RU 24969-induced locomotion in rats is mediated by 5-HT$_{1A}$ receptors, Naunyn Schmiedeberg's Arch. Pharmacol. 352:583-584.

Kenny et al., 2000, Anxiogenic effects of nicotine in the dorsal hippocampus are mediated by 5-HT$_{1A}$ and not by muscarinic M$_1$ receptors, Neuropharmacology 39:300-307.

Kenny et al., 2001, Nicotine regulates 5-HT$_{1A}$ receptor gene expression in the cerebral cortex and dorsal hippocampus, Eur. J. Neurosci. 13:1267-1271.

Killcross et al., 1997, WAY100635 and latent inhibition in the rat: selective effects at preexposure, Behav. Brain Res. 88(1):51-57.

Kishitake, 2005, Effects of 5-HT$_{1A}$-Receptor Agonist, 8-OH-DPAT, and GABA$_B$-Receptor Agonist, Baclofen, on Lordosis in Female Rats with Lesions in Either the Dorsal Raphe Nucleus or Septum, J. Pharmacol. Sci. 98:419-424.

Krebs-Thomson et al., 1996, The role of 5-HT$_{1A}$ receptors in the locomotor-suppressant effects of LSD: WAY-100635 studies of 8-OH-DPAT, DOI and LSD in rats, Behav. Pharmacol. 7:551-559.

Lin et al., 2002, Melatonin potentiates 5-HT$_{1A}$ receptor activation in rat hypothalamus and results in hypothermia, J. of Pineal Research 33:14-19.

Mcvary et al., 1997, Sexual dysfunction in the diabetic BB/WOR rat: a role of central neuropathy, Am. J. Physiol. Regul. Integr. Comp. Physiol. 272:R259-267.

Mendelson et al., 1994, 5-HT$_{1A}$ receptor agonists induce anterograde amnesia in mice through a postsynaptic mechanism, Eur. J. Pharmacol. 236:177-182.

Meneses et al., 1999, 5-HT$_{1A}$ Receptors Modulate the Consolidation of Learning in Normal and Cognitively Impaired Rats, Neurobiology of Learning and Memory 71:207-218.

Merck Manual, Sixteenth Edition, 1992, Disorders of Movement: Extrapyramidal and Cerebellar, Merck Research Laboratories, Rahway, N.J., pp. 1495-1500; see p. 1497.

Millan et al., 1998, WAY 100,635 enhances both eht 'antidepressant' actions of duloxetine and its influence on dialysate levels of serotonin in frontal cortex, Eur. J. Pharmacol. 341:165-167.

Ohno et al., 1993, Working memory deficits induced by intrahippocampal administration of 8-OH-DPAT, a 5-HT$_{1A}$ receptor agonist, in the rat, Eur. J. Pharmacol. 234:29-34.

Rasmussen et al., 1997, Nicotine withdrawal leads to increased sensitivity of serotonergic neurons to the 5-HT$_{1A}$ agonist 8-OH-DPAT, Psychopharmacology 133:343-346.

Rasmussen et al., 2000, The Novel 5-Hydroxytryptamine$_{1A}$ Antagonist LY426965: Effects on Nicotine Withdrawal and Interactions with Fluoxetine, J. Pharmacol. Exp. Therapeutics 294:688-700.

Romero et al., 1996, The 5-HT$_{1A}$ antagonist WAY-100635 selectively potentiates the presynaptic effects of serotonergic antidepressants in rat brain, Neuroscience Letters 219:123-126.

Rosen et al., 1999, Effects of SSRIs on Sexual Function: A Critical Review, J. Clin. Psychopharmacol. 19:67-85.

Schechter et al., 2002, The Potential Utility of 5-HT$_{1A}$ Receptor Antagonists in the Treatment of Cognitive Dysfunction Associated with Alzheimer's Disease, Current Pharmaceutical Design, 8:139-145.

Schecheter et al., 2005, Lecozotan (SRA-333): A selective Serotonin 1A Receptor Antagonist That Enhances the Stimulated Release of Glutamate and Acetylcholine in the Hippocampus and Possesses Cognitive-Enhancing Properties, J. of Pharmacology and Experimental Therapeutics 314:1274-1289.

Schenk, 2000, Effects of the serotonin 5-HT$_2$ antagonist, ritanserin, and the serotonin 5-HT$_{1A}$ antagonist, WAY 100635, on cocaine-seeking in rats, Pharmacol. Biochem. Behav. 67:3630369.

Smart et al., 2001, WAY-100635, a specific 5-HT$_{1A}$ antagonist, can increase the responsiveness of the mammalian circadian pacemaker to photic stimuli, Neurosci. Lett. 305:33-36.

Sramek et al., 2002, Generalised Anxiety Disorder, Treatment Options, Drugs 62(11):1635-1648.

Van Den Hooff et al., 1991, Electrophysiology of the 5-HT$_{1A}$ ligand MDL 73005EF in the rat hippocampal slice. Eur. J. Pharmacol. 196:291-298.

Vicentic et al., 1998, WAY-100635 inhibits 8-OH-DPAT-stimulated oxytocin, ACTH and corticosterone, but not prolactin secretion, Eur. J. Pharmacol. 346:261-266.

Waldinger, 2006, Emerging drugs for premature ejaculation, Expert Opin. Emerging Drugs 11:99-109.

Zhou et al., 1998, Additive Reduction of Alcohol Drinking by 5-HT$_{1A}$ Antagonist Way 200635 and Serotonin Uptake Blocker Fluoxetine in Alcohol-Preferring P Rats, Alcohol, Clin. Exp. Res. 22:266-269.

Baldwin, "Sexual Dysfunction Associated with Antidepressant Drugs", Expert Opin. Drug Saf., 3(5):457-470 (2004).

Carli et al., 1995, (S)-WAY-100135, a 5-HIT1A receptor antagonist, prevents the impairment of spatial learning caused by intrahippocampal scopolamine, European J. Pharmacology 283:133-139.

Dunlop, et al., J. Pharmacol. Tox. Methods. 40:47-55 (1998).

Hollander, et al., "Yohimbine Treatment of Sexual Side Effects Induced by Serotonin Reuptake Blockers", J. Clin Psychiatry, 53(6):207-209 (1992).

Kelly, et al., "A Randomized Double-Blind 12-Week Study of Quetiapine, Risperidone or Fluphenazine on Sexual Functioning in People with Schizophrenia", Psychoneuroendocrino, 31(3):340-346 (2006).

Newman-Tancredi, et al., "Agonist and Antagonist Actions of Antipsychotic Agents at 5-$HT_{1A}$ Receptors: a[$35_S$]GTPγS Binding Study", European Journal of Pharmacology, 355:245-256 (1998).

Norden, "Buspirone Treatment of Sexual Dysfunction Associated with Selective Serotonin Re-Uptake Inhibitors", Depression, 2:109-112 (1994).

Taylor, et al., "Strategies for Managing Antidepressant-Induced Sexual Dysfunction: Systematic Review of Randomised Controlled Trials", Journal of Affective Disorders, 88:241-254 (2005).

Wilen, et al., Tetrahedron, 33:2725 (1977).

* cited by examiner (R)-N-(2-METHYL-(4-INDOLYL-1-PIPERAZINYL)ETHYL)-N-(2-PYRIDINYL)CYCLOHEXANECARBOXAMIDE Example compound 3

N-[2-[4-(2-METHOXYPHENYL)-1-PIPERAZINYL]ETHYL]-N-(2-PYRIDINYL)CYCLOHEXANECARBOXAMIDE

Example compound 2

Example compound 1

(R)-4-Cyano-N-(2-[4-(2,3-dihydrobenzo[1,4]dioxin-5-yl)-piperazin-1-yl]-propyl]-N-pyridin-2-yl-benzamide

SEROTONERGIC AGENTS FOR TREATING SEXUAL DYSFUNCTION

This patent application is a continuation of pending application Ser. No. 11/396,307, filed on Mar. 30, 2006; which is a continuation-in-part of co-pending application Ser. No. 11/330,907, filed on Jan. 11, 2006; which is a continuation of application Ser. No. 10/441,536, filed May 20, 2003 (now U.S. Pat. No. 7,026,320); which is a continuation of application Ser. No. 10/218,251, filed on Aug. 14, 2002 (now U.S. Pat. No. 6,586,436); which is a continuation of application Ser. No. 10/010,575, filed Nov. 13, 2001 (now U.S. Pat. No. 6,469,007); which claims the benefit of provisional application Ser. No. 60/253,301, filed Nov. 28, 2000 and provisional application Ser. No. 60/297,814, filed Jun. 13, 2001, each of which is hereby incorporated by reference in their entirety.

FIELD OF THE INVENTION

The invention relates to the use of novel piperazine derivatives, their use for treating, e.g., sexual dysfunction, and to pharmaceutical compositions containing the compounds. The novel compounds are useful as $5\text{-}HT_{1A}$ binding agents, particularly as $5\text{-}HT_{1A}$ receptor antagonists.

BACKGROUND

Sexual dysfunction is associated with various drug treatments including treatments using antidepressant drugs, antipsychotic drugs, and anticonvulsant drugs. This manifestation of drug treatment is a significant cause of patient non-compliance with drug treatments. Accordingly, there is a need to identify compounds that are effective for ameliorating or preventing sexual dysfunction associated with drug treatment.

U.S. Pat. No. 6,127,357 discloses compounds of the general formula (I):

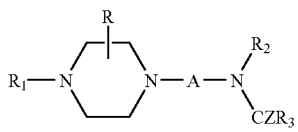

(I)

and pharmaceutically acceptable acid addition salts thereof wherein:

A is alkylene chain of 2 to 4 carbon atoms optionally substituted by one or more lower alkyl groups, Z is oxygen or sulfur, R is H or lower alkyl, $R^1$ is a mono or bicyclic aryl or heteroaryl radical, $R^2$ is a mono or bicyclic heteroaryl radical, and $R^3$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^4R^5$ [where $R^4$ is hydrogen, lower alkyl, aryl or aryl(lower)alkyl and $R^5$ is hydrogen, lower alkyl, —CO(lower)alkyl, aryl, —Coaryl, aryl(lower)alkyl, cycloalkyl, or cycloalkyl(lower)alkyl or $R^4$ and $R^5$ together with the nitrogen atom to which they are both attached represent a saturated hytrocyclic ring which may contain a further heteroatom], or a group of formula $OR^6$ [where $R^6$ is lower alkyl, cycloalkyl, cycloalkyl(lower)alkyl, aryl, aryl(lower)alkyl, heteroaryl or heteroaryl(lower)alkyl].

WO 97/03982 discloses compounds of the general formula (II):

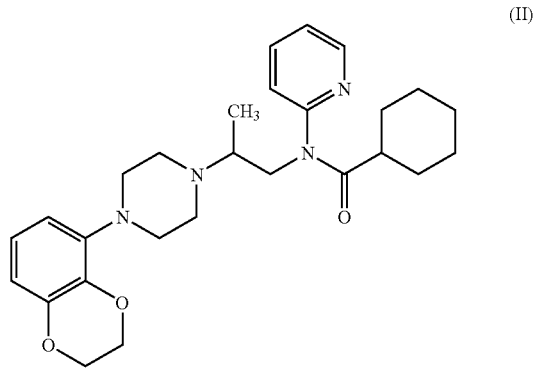

(II)

including enantiomers and the pharmaceutically acceptable acid addition salts thereof.

The compounds of formula (II) fall within the disclosure of U.S. Pat. No. 6,127,357 but are not specifically disclosed therein. Compounds of Formula II were taught to have potent $5\text{-}HT_{1A}$ antagonist activity in vivo when administered by the oral route.

SUMMARY

It has been found that compounds that are $5\text{-}HT_{1A}$ receptor antagonists are useful for treating sexual dysfunction, e.g., sexual dysfunction associated with drug treatment such as drug treatment with an antidepressant, an antipsychotic, or an anticonvulsant. Accordingly, the invention relates to a method for treating sexual dysfunction associated with drug treatment in a patient in need thereof. The method includes administering to the patient an effective amount of a compound that is a $5\text{-}HT_{1A}$ antagonist. In some embodiments, the drug treatment is antidepressant drug treatment, antipsychotic drug treatment, or anticonvulsant drug treatment. The compound can be a compound of formula (I),

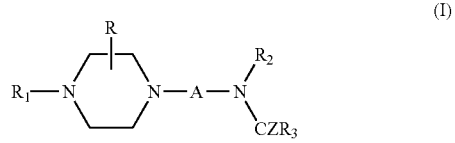

(I)

or a pharmaceutically acceptable acid addition salt thereof such that

A is alkylene chain of 2 to 4 carbon atoms optionally substituted by one or more lower alkyl groups, Z is oxygen or sulfur, R is H or lower alkyl, $R^1$ is a mono or bicyclic aryl or heteroaryl radical, $R^2$ is a mono or bicyclic heteroaryl radical, and $R^3$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^4R^5$ [where $R^4$ is hydrogen, lower alkyl, aryl or aryl(lower)alkyl and $R^5$ is hydrogen, lower alkyl, —CO(lower)alkyl, aryl, —Coaryl, aryl(lower)alkyl, cycloalkyl, or cycloalkyl(lower)alkyl or $R^4$ and $R^5$ together with the nitrogen atom to which they are both attached represent a saturated hytrocyclic ring which may contain a further heteroatom], or a group of formula $OR^6$ [where $R^6$ is lower alkyl, cycloalkyl, cycloalkyl(lower)alkyl, aryl, aryl(lower)alkyl, heteroaryl or heteroaryl(lower)alkyl].

In other embodiments, the compound is a compound of formula (III), as described herein or a pharmaceutically acceptable salt thereof. In yet other embodiments, the compound is a compound of formula (IV) as described herein.

The compound can be (R)-4-cyano-N-{2-[4-(2,3-dihydro-benzo[1,4]dioxin-5-yl)-piperazin-1-yl]propyl}-N-pyridin-2-yl-benzamide or a pharmaceutically acceptable acid addition salt thereof (Example compound 1), N-[2-[4-(2-methoxyphenyl)-1-piperazinyl]ethyl]-N-(2-pyridinyl)cyclohexanecarboxamide (Example compound 2) or a pharmaceutically acceptable acid addition salt thereof, or (R)-N-(2-methyl-(4-indolyl-1-piperazinyl)ethyl)-N-(2-pyridinyl)cyclohexanecarboxamide (Example compound 3) or a pharmaceutically acceptable acid addition salt thereof.

In certain embodiments of the invention the drug associated with sexual dysfunction is a selective serotonin reuptake inhibitor (SSRI) (for example, fluoxetine, citolopram, escitalopram oxalate, fluvoxamine maleate, paroxetine, or sertraline), a tricyclic antidepressant (for example, desipramine, amitriptiyline, amoxipine, clomipramine, doxepin, imipramine, nortriptyline, protriptyline, or trimipramine, an aminoketone class compound (for example, bupropion). In some embodiments, the drug is a monoamine oxidase inhibitor (MAOI) (for example, phenelzine), a serotonin and norepinepherine reuptake inhibitor (SNRI) (for example, venlafaxine, nefazodone, milnacipran, duloxetine), a norepinephrine reuptake inhibitor (NRI) (for example, reboxetine), a partial $5\text{-HT}_{1A}$ agonist (for example, buspirone), a $5\text{-HT}_{2A}$ receptor antagonist (for example, nefazodone), a typical antipsychotic drug, or an atypical antipsychotic drug. Examples of such antipsychotic drugs include aliphatic phethiazine, a piperazine phenothiazine, a butyrophenone, a substituted benzamide, and a thioxanthine. Additional examples of such drugs include haloperidol, olanzapine, clozapine, risperidone, pimozide, aripiprazol, and ziprasidone. In some cases, the drug is an anticonvulsant, e.g., phenobarbital, phenytoin, primidone, or carbamazepine. In some cases, the patient in need of treatment for sexual dysfunction is being treated with at least two drugs that are antidepressant drugs, antipsychotic drugs, anticonvulsant drugs, or a combination thereof.

In certain embodiments, the invention includes oral delivery of the compound for treating sexual dysfunction. The compound can be, in some cases, delivered as a sustained release compound sustained release compound. In other embodiments of the invention, the sexual dysfunction comprises a deficiency in penile erection.

The invention also relates to a method of improving sexual function in a patient in need thereof. The method includes administering to the patient a pharmaceutically effective amount of a compound that is a $5\text{-HT}_{1A}$ antagonist. In some embodiments, the compound is a compound of formula (I)

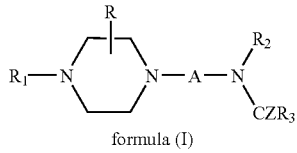

formula (I)

or a pharmaceutically acceptable acid addition salt thereof, wherein

A is alkylene chain of 2 to 4 carbon atoms optionally substituted by one or more lower alkyl groups, Z is oxygen or sulfur, R is H or lower alkyl, $R^1$ is a mono or bicyclic aryl or heteroaryl radical, $R^2$ is a mono or bicyclic heteroaryl radical, and $R^3$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^4R^5$ [where $R^4$ is hydrogen, lower alkyl, aryl or aryl(lower)alkyl and $R^5$ is hydrogen, lower alkyl, —CO(lower)alkyl, aryl, —Coaryl, aryl(lower)alkyl, cycloalkyl, or cycloalkyl(lower)alkyl or $R^4$ and $R^5$ together with the nitrogen atom to which they are both attached represent a saturated hytrocyclic ring which may contain a further heteroatom], or a group of formula $OR^6$ [where $R^6$ is lower alkyl, cycloalkyl, cycloalkyl(lower)alkyl, aryl, aryl(lower)alkyl, heteroaryl or heteroaryl(lower)alkyl]; or formula (III)

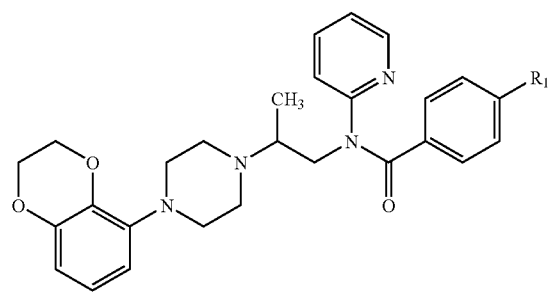

such that $R_1$ is cyano, nitro, trifluoromethyl or halogen, or a pharmaceutically acceptable acid addition salt thereof; or formula (IV)

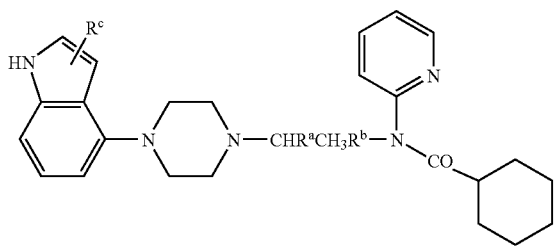

such that, Ra and Rb are each hydrogen or methyl and Rc is hydrogen, halo or C1-4 alkyl; or a pharmaceutically acceptable acid addition salt thereof. In some embodiments, of the method, the compound is Example compound 1, Example compound 2, or Example compound 3.

In another aspect, the invention relates to a pharmaceutical composition for treating sexual dysfunction associated with drug treatment, the composition including a compound of formula (I), formula (III), or formula (IV). In some embodiments, the drug is an antidepressant, an antipsychotic, or an anticonvulsant. In other embodiments, the compound is effective for ameliorating sexual dysfunction in an animal model of sexual dysfunction associated with drug treatment, for example, in an animal model of sexual dysfunction that is an antidepressant drug-induced model of sexual dysfunction.

Yet another aspect of the invention relates to a package comprising a $5\text{-HT}_{1A}$ antagonist and instructions, such that the instructions comprise instructions for treating sexual dysfunction, e.g., the instructions are for treating sexual dysfunction associated with drug treatment.

In another aspect, the invention relates to a method for treating memory deficits or cognitive disorders; treating alcohol, nicotine, or drug withdrawal; treating Parkinson's disease or motor disorders; treating migraine; treating eating disorders; treating sexual dysfunction; treating urinary incontinence, treating stroke; treating endocrine disorders; treating sleep disorders; treating attention deficit disorders; treating Tourette's syndrome, autism, social phobias, hyperactivity disorders or thermoregulatory disorders in a patient in need thereof, comprising providing to the patient a therapeutically effective amount of a compound of formula (III):

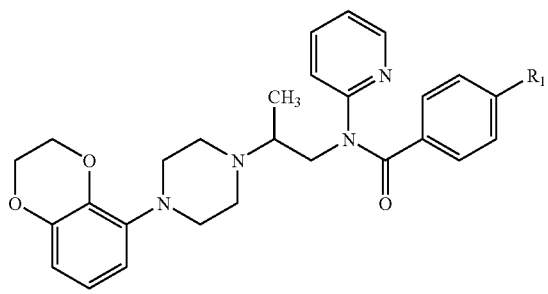

(III)

wherein $R_1$ is cyano, nitro, trifluoromethyl or halogen, or pharmaceutically acceptable acid addition salts thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION OF THE INVENTION

Novel compounds of the invention have the structural formula (III):

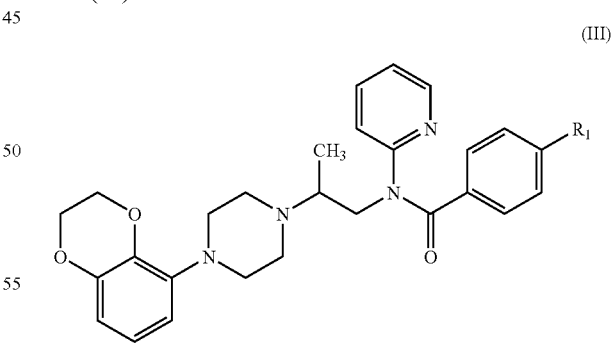

(III)

wherein $R_1$ is cyano, nitro, trifluoromethyl or halogen, or pharmaceutically acceptable acid addition salts thereof.

Halogen, as used herein, refers to chlorine, fluorine, bromine and iodine.

The compounds of Formula III contain an asymmetric carbon atom. Accordingly, they may exist in different stereoisomeric forms. In some embodiments, the (R) stereoisomer having the formula (IIIa) is used.

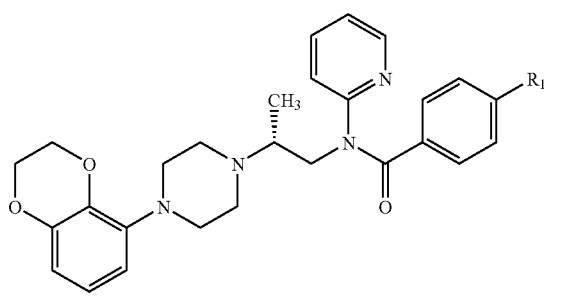

(IIIa)

In accordance with some embodiments of the invention, the (R) stereoisomer is substantially free of the (S) stereoisomer. Substantially free, as used herein, means that the compound is made up of a significantly greater proportion of its (R) stereoisomer than the (S) stereoisomer. In certain embodiments, the compound is made up of at least about 90% by weight of its (R) stereoisomer and about 10% by weight or less of its (S) stereoisomer. In other embodiments of the invention, the compound is made up of at least about 99% by weight of its (S) stereoisomer and about 1% by weight or less of the (R) stereoisomer. In some cases, stereoisomers may be isolated from racemic mixtures by any method known to those skilled in the art, including high performance liquid chromatography (HPLC) and the formation and crystallization of chiral salts. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Examples of compounds useful for treating sexual dysfunction such as sexual dysfunction associated with the use of a drug such as an antidepressant drug, antipsychotic drug, or anticonvulsant drug include, compounds disclosed in U.S. Pat. No. 6,127,357 (compounds of formula (I); compounds disclosed in WO 95/33725; compounds disclosed in WO 95/33743 such as compounds of formula (IV), (IV)

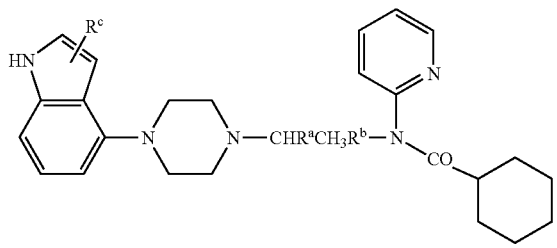

wherein, Ra and Rb are each hydrogen or methyl and Rc is hydrogen, halo or C1-4 alkyl; or a pharmaceutically acceptable acid addition salt thereof; and compounds disclosed herein.

Figure 6:
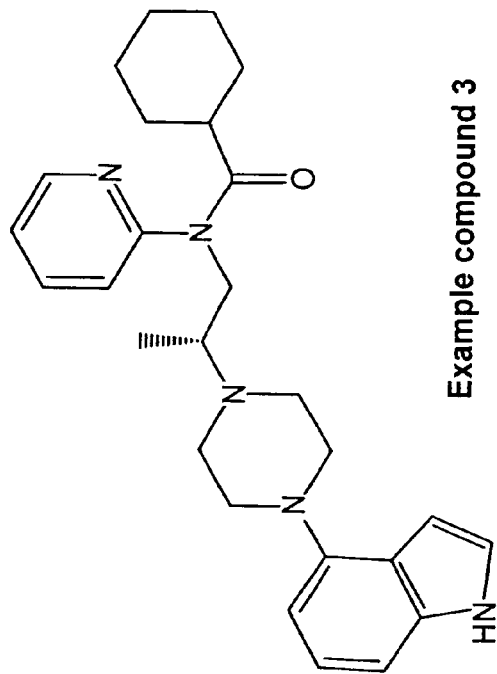
FIG. 6 is a drawing representing the chemical structures of Example compound 1, Example compound 2, and Example compound 3.
Figure 6:
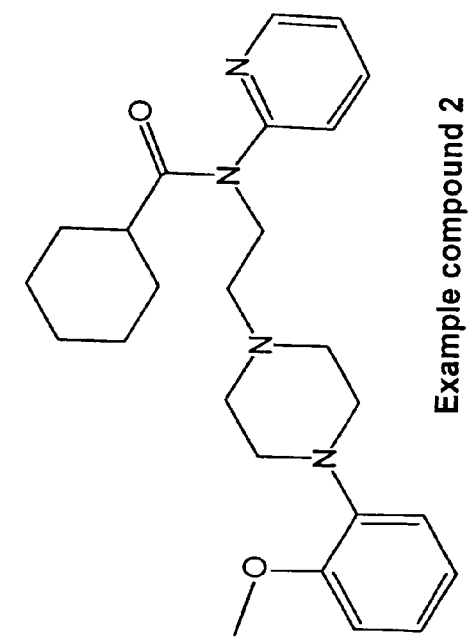
Figure 6:
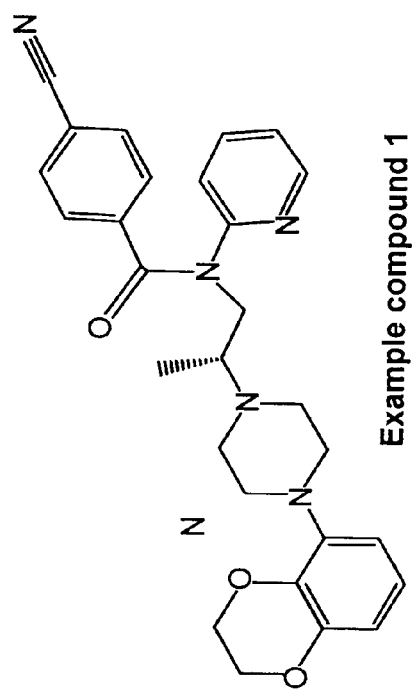

Useful compounds are those that exhibit activity as $5\text{-HT}_{1A}$ antagonists and can inhibit or prevent sexual dysfunction (e.g., as shown using an animal model of sexual dysfunction due to administration of a drug). Non-limiting examples of compounds useful in the invention are (R)-4-cyano-N-{2-[4-(2,3-dihydro-benzo[1,4]dioxin-5-yl)-piperazin-1-yl]pro-pyl}-N-pyridin-2-yl-benzamide and pharmaceutically acceptable acid addition salts thereof (Example compound 1), N-[2-[4-(2-methoxyphenyl)-1-piperazinyl]ethyl]-N-(2-pyridinyl)cyclohexanecarboxamide (Example compound 2) and pharmaceutically acceptable acid addition salts thereof, and (R)-N-(2-methyl-(4-indolyl-1-piperazinyl)ethyl)-N-(2-pyridinyl)cyclohexanecarboxamide (Example compound 3) and pharmaceutically acceptable acid addition salts thereof (FIG. 6).

The pharmaceutically acceptable salts are generally the acid addition salts which can be formed from a compound of a general formula described herein and a pharmaceutically acceptable acid such as, for example, benzoic, phosphoric, sulfuric, hydrochloric, hydrobromic, citric, maleic, malic, mandelic, mucic, nitric, fumaric, succinic, tartaric, acetic, lactic, pamoic, pantothenic, benzenesulfonic, or methanesulfonic acid. In some embodiments of the invention the acid addition salt is hydrochloric acid. Other pharmaceutically acceptable salts known to those in the art can be used.

The compounds of the present invention can be prepared by known methods from known starting materials that are available by conventional methods. For example the compounds may be prepared by the general methods disclosed in EP-A-0512755 and WO 97/03982.

Such disclosed methods include acylating an amine of formula (IV) with a known benzoyl chloride (V) or an alternative acylating derivative thereof. Examples of acylating derivatives include the acid anhydride, imidazolides (e.g., obtained form carbonyldiimidazole), or activated esters.

(IV)

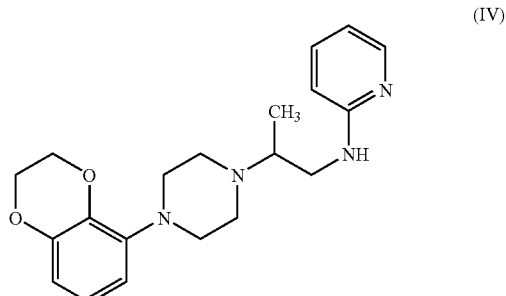

(V)

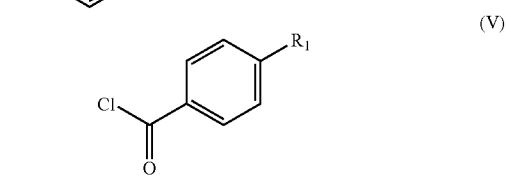

wherein $R_1$ is cyano, halogen, trifluoromethyl or nitro.

Novel compounds of the present invention are potent $5\text{-HT}_{1A}$ binding agents that selectively bind to the $5\text{-HT}_{1A}$ receptor. Furthermore, the novel compounds of the invention are $5\text{-HT}_{1A}$ receptor antagonists when tested by standard pharmacological procedures.

In addition, the novel compounds of formula (III) are unique from previously disclosed $5\text{-HT}_{1A}$ receptor antagonists in that they possess a superior duration of action as a $5\text{-HT}_{1A}$ receptor antagonist when administered in vivo.

EXAMPLES

The present invention is illustrated by reference to the following examples and additional information. The examples of experiments are provided for illustrative purposes only. They are not to be construed as limiting the scope or content of the invention in any way. Those skilled in the art of organic synthesis may be aware of still other synthetic routes to the invention compound. The reagents and intermediates used herein are either commercially available or prepared according to standard literature procedures.

Methods of testing the effect of an invention compound on sexual dysfunction are described infra. Such methods are useful for identifying 5-HT$_{1A}$ antagonists (i.e., 5-HT$_{1A}$ receptor antagonists) that are effective for treating sexual dysfunction. Other methods of testing the effect of a compound on sexual dysfunction are known in the art and include, e.g., paired mating observations (for example, of mounting, mount attempts, intromission, mount frequency, ejaculation, mount with intromission, ejaculation latency, intromission frequency, copulation efficiency, anogenital sniffing, or post-ejaculatory interval), or assay of penile erections (e.g., determining intracavernosal blood pressure or observation of non-contact penile erections in sexually naïve male rats).

Example 1

(R)-4-Cyano-N-{2-[4-(2,3-Dihydro-Benzo[1,4]dioxin-5-yl)-Piperazin-1-yl]-Propyl}-N-Pyridin-2-yl-Benzamide (Example Compound 1)

A solution of {(R)-2-[4-(2,3-dihydrobenzo[1,4]dioxin-5-yl)piperazin-1-yl]propyl}-pyridin-2-ylamine (0.846 g, 2.38 mmol) in dichloromethane (20 mL) was treated at 0° C. with the dropwise addition of a dichloromethane solution of 4-cyanobenzoyl chloride (1.1 equivalents, 2.63 mmol in 5 mL). After stirring for 16 hours the mixture was poured onto hexane (100 mL) to precipitate the titled compound as its monohydrochloride salt (white solid, 1.2 g, 97% yield), which was recrystallized from dichloromethane/hexane.

MS (+) 484 (M+H)$^+$. m.p. 239-240° C. [α]25/D=+56 (c=0.6, MeOH) Elemental Analysis for: $C_{28}H_{29}N_5O_3 \cdot 1.0$ HCl Calculated: C, 64.67; H, 5.81; N, 13.47: Found: C, 64.69; H, 5.93; N, 13.52:

In order to demonstrate the superior duration of action of the compounds of formula (III), Example 1 was compared to representative compounds of U.S. Pat. No. 6,127,357 and WO 97/03892.

Representative compounds of U.S. Pat. No. 6,127,357 possess a cyclohexylamide moiety and a 2-methoxyphenylpiperazine grouping. The most potent example of this general structure (and the most potent compound taught in U.S. Pat. No. 6,127,357) is compound A, described as "Example 3" in U.S. Pat. No. 6,127,357. The only other class of compounds in U.S. Pat. No. 6,127,357 for which data are given is that which possess a cyclohexylamide moiety and a benzodioxinylpiperazine grouping ("Example 17" in U.S. Pat. No. 6,127,357). A small subset of this class of compounds is specifically claimed in WO97/03892, with the preferred compound being compound B ("Example A1" in WO97/03892). Therefore, these two preferred examples from EP-A-0512755 and WO 97/03892 have been chosen as representatives for comparison to the compounds of formula (III).

Compound A

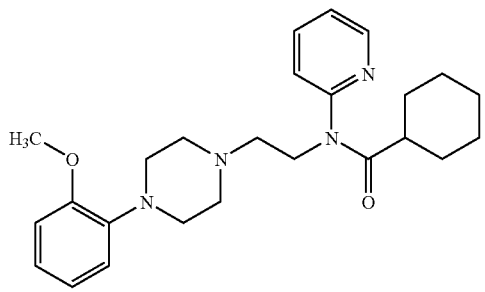

("Example 3" from U.S. Pat. No. 6,127,357)

-continued

Compound B

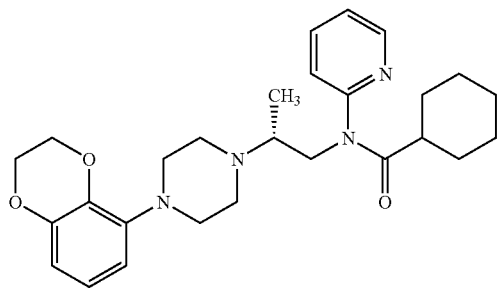

("Example A1" from WO 97/03892)

Example 2

Binding Profile

Compounds were tested for binding to cloned human 5-HT$_{1A}$ receptors stably transfected into CHO cells using [$^3$H] 8-OH-DPAT as the 5-HT$_{1A}$ radioligand (according to general procedure described in J. Dunlop et al., *J. Pharmacol. Tox. Methods*, 40, 47-55 (1998)). As shown in Table 1, compounds of the present invention display high affinity for the 5-HT1A receptor.

Example 3

In Vitro Functional Activity

A clonal cell line stably transfected with the human 5-HT$_{1A}$ receptor was utilized to determine the intrinsic activity of compounds (according to the general procedure described in J. Dunlop et al., *J. Pharmacol. Tox. Methods*, 40, 47-55 (1998)). Data are provided in Table 1. As shown in Table 1, compounds of the present invention antagonized the ability of 10 nM 8-OH-DPAT to inhibit forskolin-stimulated cAMP production in a concentration-related fashion.

TABLE 1

| Compound | 5-HT$_{1A}$ Affinity Ki (nM) | 5-HT$_{1A}$ Antagonist Activity cAMP Assay IC$_{50}$ (nM) |
|---|---|---|
| Example 1 | 1.6 | 25 |
| Compound A | 0.96 | 7 |
| Compound B | 0.97 | 20 |

Example 4

In Vivo Functional Activity

The ability of the compounds to function in vivo as 5-HT$_{1A}$ antagonists was assessed in rats using a Fixed Responding Model (D. Blackman, in "Operant Conditioning: An Experimental Analysis of Behavior", J. Butcher, ed., Methuen and Co., Ltd., London). In this model rats are trained to respond (lever pressing) under a fixed-ratio 30 schedule of food presentation in order to receive a food pellet reinforcer. Administration of the 5-HT$_{1A}$ agonist 8-OH-DPAT reduces the control response rate (assessed by administration of vehicle placebo). The 5-HT$_{1A}$ antagonist activity of a test compound is determined by measuring its ability to antagonize this agonist-induced decrease in response rate. A full antagonist effect is considered one in which the test compound completely reverses the agonist-induced response rate, returning it to control levels. The data given in Table 2 demonstrate that a 1 mg/kg dose of the compound of Example 1 completely reverses the decrease in response rate induced by administration of a 0.3 mg/kg dose of 8-OH-DPAT. Thus, compounds of the present invention function as $5\text{-HT}_{1A}$ antagonists in vivo.

TABLE 2

Response Rate (responses/second)

| Vehicle (Control) | 8-OH-DPAT (0.3 mg/kg sc) | 8-OH-DPAT (0.3 mg/kg sc) + Example compound 1 (1 mg/kg sc) |
|---|---|---|
| 2.4 ± 0.5 | 0.5 ± 0.2 | 2.5 ± 0.2 |

Example 5

Duration of Action In Vivo

The duration of action in the Fixed Responding Model was assessed by pre-treating animals with test compound and then challenging with a 0.3 mg/kg dose of the $5\text{-HT}_{1A}$ agonist 8-OH-DPAT at various time intervals after the administration of test compound. All drug and vehicle administrations were made by the subcutaneous route. Doses of the test compounds selected for comparison were those that caused a ten-fold shift in the 8-OH-DPAT dose-response curve when administered 30 minutes prior to agonist. The doses selected for the duration of action comparison are listed in Table 3.

TABLE 3

| Test Compound | Dose Which Shifts Agonist Dose-response Curve by 10-fold (mg/kg, sc) |
|---|---|
| Compound A (FIG. 1) | 0.03 |
| Compound B (FIG. 1) | 0.1 |
| Example 1 | 1.0 |

Data are presented for pre-treatment of the animals with test compound at 0.5 hours, 2 hours, and 4 hours prior to administration of a 0.3 mg/kg dose of 8-OH-DPAT. Results are normalized to control values, with 100% being the control response rate observed when vehicle is administered rather than the agonist 8-OH-DPAT.

TABLE 4

| | % Response Rate | | |
|---|---|---|---|
| Compound | 0.5 hour pretreatment | 2 hour pretreatment | 4 hour pretreatment |
| Compound A + 8-OH-DPAT | 90 ± 3 | 55 ± 28 | 41 ± 26 |
| Control + 8-OH-DPAT | 23 ± 9 | 3 ± 1 | 3 ± 1 |
| Compound B + 8-OH-DPAT | 100 ± 11 | 71 ± 12 | 27 ± 14 |
| Control + 8-OH-DPAT | 21 ± 9 | 42 ± 6 | 42 ± 6 |
| Example compound 1 + 8-OH-DPAT | 100 ± 7 | 118 ± 13 | 99 ± 16 |

TABLE 4-continued

| | % Response Rate | | |
|---|---|---|---|
| Compound | 0.5 hour pretreatment | 2 hour pretreatment | 4 hour pretreatment |
| Control + 8-OH-DPAT | 29 ± 6 | 35 ± 10 | 35 ± 10 |

As can be seen from Table 4, all three test compounds (Compound A, B, and Example compound 1) completely antagonize the agonist-induced decrease in responding 30 minutes after their administration, returning the response rate to control levels. However, when agonist is given 2 hours following test drug administration (Column 3), the $5\text{-HT}_{1A}$ antagonist effects of compounds A and B no longer return the response rate to control levels while Example compound 1 still displays complete $5\text{-HT}_{1A}$ antagonist effects. By four hours post-administration (Column 4), the $5\text{-HT}_{1A}$ antagonist effects of Compounds A and B are completely lost, while Example compound 1 continues to provide complete antagonism of the agonist-induced decrease in response rate. Thus, the duration of action of Example compound 1 is longer than 4 hours, while those of Compounds A and B are somewhere between 30 minutes and 2 hours.

The increased duration of action of the novel compounds of the present invention, compared to that of the classes of compounds disclosed in U.S. Pat. No. 6,127,357 and WO 97/03892 is particularly advantageous in that a smaller number of doses of the compound can be administered to produce a similar therapeutic effect.

Compounds of the present invention may be used to treat a subject suffering from CNS disorders such as schizophrenia, (and other psychotic disorders such as paranoia and manodepressive illness), Parkinson's disease and other motor disorders, anxiety (e.g., generalized anxiety disorders, panic attacks, and obsessive compulsive disorders), depression (such as by the potentiation of serotonin reuptake inhibitors and serotonin norepinephrine reuptake inhibitors), Tourette's syndrome, migraine, autism, attention deficit disorders and hyperactivity disorders. Compounds of the present invention may also be useful for the treatment of sleep disorders, social phobias, pain, thermoregulatory disorders, endocrine disorders, urinary incontinence, vasospasm, stroke, eating disorders such as for example obesity, anorexia and bulimia, sexual dysfunction, and the treatment of alcohol, drug and nicotine withdrawal.

Compounds of the present invention including those disclosed herein and those disclosed in U.S. Pat. No. 6,127,357 and WO 95/33743 are useful for treating sexual dysfunction, e.g., sexual dysfunction associated with a drug treatment. Sexual dysfunction can be in a male or female subject. The condition can include erectile dysfunction as well as disorders of arousal, motivation, desire, decreased libido, anorgasmia, delayed ejaculation, premature ejaculation, and sexual anxiety disorders, sexual pain disorders, sexual aversion disorders. The cause can be undefined or can be due to a known cause, e.g., substance-related sexual dysfunction.

Drugs associated with sexual dysfunction that can be treated as described herein include antidepressant drugs (antidepressants). Such antidepressant drugs include, for example, serotonin reuptake inhibitors (SRIs), norepinephrine reuptake inhibitors (NRIs), combined serotonin-norepinephrine reuptake inhibitors (SNRIs), monoamine oxidase inhibitors (MAOIs), reversible inhibitors of monoamine oxidase (RIMAs), phosphodiesterase-4 (PDE4) inhibitors, corticotropin releasing factor (CRF) antagonists (e.g., compounds described in International Patent Specification Nos. WO 94/13643, WO 94/13644, WO 94/13661, WO 94/13676 and WO 94/13677), alpha.-adrenoreceptor antagonists, atypical antidepressants (e.g., buproprion, lithium, nefazodone, trazodone, viloxazine, and pharmaceutically acceptable salts thereof, and sibutramine). Additional examples of such antidepressants include triple uptake inhibitors such as DOV 216303 and DOV 2194; melatonin agonists such as agomelotine, super neurotransmitter uptake blockers (SNUBs; e.g., NS-2389 from GlaxoSmithKline and Neurosearch; (R)-DDMA from Sepracor), and substance P/neurokinin receptor antagonists (e.g., aprepitant/MK-869 from Merck; NKP-608 from Novartis; CPI-122721 from Pfizer; R673 from Roche; TAK637 from Takeda; and GW-97599 from GlaxoSmithKline).

Another class of antidepressant agents that may be associated with sexual dysfunction that can be treated as described herein is noradrenergic and specific serotonergic antidepressants (NaSSAs).

Examples of NRIs include tertiary amine tricyclics and secondary amine tricyclics. Specific examples of tertiary amine tricyclics include, without limitation, amitriptyline, clomipramine, doxepin, imipramine and trimipramine, and pharmaceutically acceptable salts thereof. Suitable examples of secondary amine tricyclics include, without limitation, amoxapine, desipramine, maprotiline, nortriptyline and protriptyline, and pharmaceutically acceptable salts thereof. Another NRI that may be associated with sexual dysfunction is reboxetine (2-[.alpha.-(2-ethoxy)phenoxy-benzyl]morpholine), usually administered as the racemate.

SSRIs that may be associated with sexual dysfunction that can be treated using compounds and methods described herein include, without limitation, citalopram (1-[3-(dimethylamino)propyl]-(4-fluorophenyl)-1,3-dihydr-o-5-isobenzofurancarbonitrile; fluoxetine (N-methyl-3-(p-trifluoromethylphenoxy)-3-phenylpropylamine, marketed in the hydrochloride salt form and as the racemic mixture of its two isoforms; fluoxetine/olanzapine in combination; fluvoxamine (5-methoxy-1-[4-(trifluoromethyl)phenyl]-1-pentanone O-(2-aminoethyl)oxime; paroxetine (trans-(–)-3-[(1,3-benzodioxol-5-yloxy)methyl]-4-(4-fluorophenyl)piperidine); sertraline, (1S-cis)-4-(3,4-dichlorophenyl)-1,2,3,4-tetrahydro-N-methyl-1-naphthylamine hydrochloride; escitalopram; new 5HT1A agonists variza, alnespirone, gepirone, sunepitron, MKC242, vilazodone, eptapirone, and ORG12962 from Organon; and pharmaceutically acceptable salts thereof.

MAOIs that may be associated with sexual dysfunction that can be treated using the methods and compounds disclosed herein include, without limitation, isocarboxazid, phenelzine, selegiline and tranylcypromine, and pharmaceutically acceptable salts thereof. Reversible MAOIs that may be associated with sexual dysfunction include, without limitation, moclobemide (4-chloro-N-[2-(4-morpholinyl)-ethyl] benzamide; selegiline, and pharmaceutically acceptable salts thereof.

SNRIs that can be associated with sexual dysfunction that can be treated as described herein include, without limitation, venlafaxine and pharmaceutically acceptable salts and analogs, including the O-desmethylvenlafaxine succinate salt; milnacipran (N,N-diethyl-2-aminomethyl-1-phenylcyclopropanecarboxamide; mirtazapine; nefazodone; duloxetine; and pharmaceutically acceptable salts thereof.

Examples of specific antidepressants that can be associated with sexual dysfunction suitable for treatment using a compounds and methods described herein include, without limitation, adinazolam, alaproclate, alnespirone, amineptine, amitriptyline, amitriptyline/chlordiazepoxide combination, amoxapine, aprepitant, atipamezole, azamianserin, bazinaprine, befuraline, bifemelane, binodaline, bipenamol, brofaromine, buproprion, caroxazone, cericlamine, cianopramine, cimoxatone, citalopram, clemeprol, clomipramine, clovoxamine, dazepinil, deanol, demexiptiline, desipramine, O-desmethylvenlafaxine, dibenzepin, dothiepin, doxepin, droxidopa, duloxetine, elzasonan, enefexine, eptapirone, escitalopram, estazolam, etoperidone, femoxetine, fengabine, fezolamine, fluotracen, fluoxetine, fluvoxamine, gepirone, idazoxan, imipramine, indalpine, indeloxazine, iprindole, isocarboxazid, levoprotiline, litoxetine, lofepramine, maprotiline, medifoxamine, metapramine, metralindole, mianserin, milnacipran, minaprine, mirtazapine, moclobemide, montirelin, nebracetam, nefopam, nefozodine, nemititide, nialamide, nomifensine, norfluoxetine, nortriptyline, orotirelin, oxaflozane, paroxetine, pheneizine, pinazepam, pirlindone, pizotyline, protryptiline, reboxetine, ritanserin, robalzotan, rolipram, selegiline, sercloremine, sertraline, setiptiline, sibutramine, sulbutiamine, sulpiride, sunepitron, teniloxazine, thozalinone, thymoliberin, tianeptine, tiflucarbine, tofenacin, tofisopam, toloxatone, tomoxetine, tranylcypromine, trazodone, trimiprimine, venlafaxine, veralipride, vilazodone, viloxazine, viqualine, zimelidine and zometrapine, and pharmaceutically acceptable salts thereof, and St. John's wort herb, or *Hypencuin perforatum*, or extracts thereof.

In some cases, anti-anxiety agents are associated with sexual dysfunction, which can be treated using compounds and methods described herein. Such anti-anxiety agents may include, without limitation, neurokinin receptor (NK) antagonists (e.g., saredutant and osanetant) and corticotropin releasing factor (CRF) antagonists.

Antipsychotic drugs are also associated with sexual dysfunction that can be treated using a $5\text{-HT}_{1A}$ antagonist as described herein. Such drugs include, without limitation, a typical or atypical antipsychotic drug, for example, an aliphatic phethiazine, a piperazine phenothiazine, a butyrophenone, a substituted benzamide, or a thioxanthine. Additional examples of such drugs include amisulpiride, aripiprazole, chlorpromazine, clozapine, fluphenazine, haloperidol, loxapine, mesoridazine, molindone, olanzapine, perphenazine, pimozide, quetiapine, risperidone, seroquel, supiride, thioridazine, thiothixene, trifluoperazine, ziprasidone, and (S)-2-(benzylamino-methyl)-2,3,8,9-tetrahydro-7H-1,4-dioxino [2,3-e]indol-8-one, a D2 partial agonist, that is disclosed in U.S. Pat. No. 5,756,532; or pharmaceutically acceptable salts thereof.

$5\text{-HT}_{1A}$ receptor antagonists are also useful for treating sexual dysfunction in patients being treated with a combination of drugs, e.g., a combination of one or more antidepressant and antipsychotic compounds. Anticonvulsant treatment is also associated with sexual dysfunction that can be treated with compounds disclosed herein. Examples of anticonvulsants associated with sexual dysfunction include phenobarbital, phenytoin, primidone, and carbamazepine.

Compounds of the present invention are also useful for the treatment of cognitive dysfunction. Thus, compounds of the present invention may be useful for the treatment of cognitive dysfunction associated with mild cognitive impairment (MCI) Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

"Provided", as used herein with respect to providing a compound or substance covered by this invention, means either directly administering such a compound or substance, or administering a prodrug, derivative, or analog which will form an equivalent amount of the compound or substance within the body. Prodrugs can be prepared such as described in *Design of Prodrugs*, Bundgaard, H. ed., (Elsevier, New York 1985); *Prodrugs as Novel Drug Delivery Systems*, Higuchi, T and Stella, V. eds, (American Chemical Society, Washington, D.C. 1975); *Design of Biopharmaceutical Properties through Prodrugs and Analogs*, Roche, E. ed., (American Pharmaceutical Association Academy of Pharmaceutical Sciences, Washington, D.C., 1977); and Metabolic Considerations in Prodrug Design, Balant, L. P. and Doelker, E. in *Burger's Medicinal Chemistry amd Drug Discovery*, Fifth Edition, Wolff, M., ed, Volume 1, pages 949-982, (John Wiley & Sons, Inc. 1995).

Compounds as described herein are useful for the preparation of a medicament for use in treating a sexual disorder, e.g., a sexual disorder associated with use of a drug such as an antidepressant drug, an antipsychotic drug, an anticonvulsant drug, or a combination of one or more of such drugs.

The compounds of the present invention may be administered orally or parentally, neat or in combination with conventional pharmaceutical carriers. Applicable solid carriers can include one or more substances which may also act as flavoring agents, lubricants, solubilizers, suspending agents, fillers, glidants, compression aids, binders, tablet-disintegrating agents or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example and without limitation, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions that are sterile solutions or suspensions can be utilized by, for example, intramuscular, intraperitoneal or subcutaneous injection. Sterile solutions can also be administered intravenously. Oral administration may be either in liquid or solid composition form. Preferably, the pharmaceutical compositions containing the present compounds are in unit dosage form, e.g., as tablets or capsules. In such form, the composition is subdivided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a capsule or tablet itself, or it can be the appropriate number of any such compositions in package form. The therapeutically effective dosage to be used may be varied or adjusted by the physician and generally ranges from 0.5 mg to 750 mg, according to the specific condition(s) being treated and the size, age and response pattern of the patient. A packaged composition can also include instructions for use, e.g., to treat a pre-existing condition of sexual dysfunction or to prevent or ameliorate an anticipated condition of sexual dysfunction such as sexual dysfunction associated with a drug treatment (e.g., treatment with an antidepressant such as an SSRI, an antipsychotic drug, or an anticonvulsant drug).

Example 6

Treatment of Sexual Dysfunction

An animal model was used to demonstrate the utility of treating or preventing sexual dysfunction, e.g., sexual dysfunction associated with SSRI treatment, with a compound that can act as a $5\text{-HT}_{1A}$ antagonist. The animal model is based on the finding that sexually experienced rats that are administered an SSRI, a drug used to treat certain conditions such as depression, display a reduction in the number of non-contact penile erections. SSRI treatment is associated with sexual dysfunction in human subjects. In general, the animal model exposes sexually experienced male rats (Sprague-Dawley rats) to female rats in estrous in a novel testing arena that is not the regular housing environment. The number of non-contact penile erections is assayed over a specified test period, e.g., 30 minutes (Sukoff Rizzo et al., 2006, Society for Neuroscience Abst. #559.4; U.S. Provisional Application Ser. No. 60/682,3379, filed May 19, 2005). In the experiments described herein, animals were generally treated either with 0.9% saline (vehicle) or a drug in the vehicle.

The ability of various drugs associated with sexual dysfunction in humans to cause sexual dysfunction in the animal model was tested using three different drugs, bupropion (20 mg/kg), desipramine (10 mg/kg), and fluoxetine (10 mg/kg), or vehicle alone (0.9% saline), each administered intraperitoneally (i.p.), once per day for 14 days. After the treatment period, animals were tested for the frequency of non-contact penile erections over a 30 minute trial period.

Figure 1:
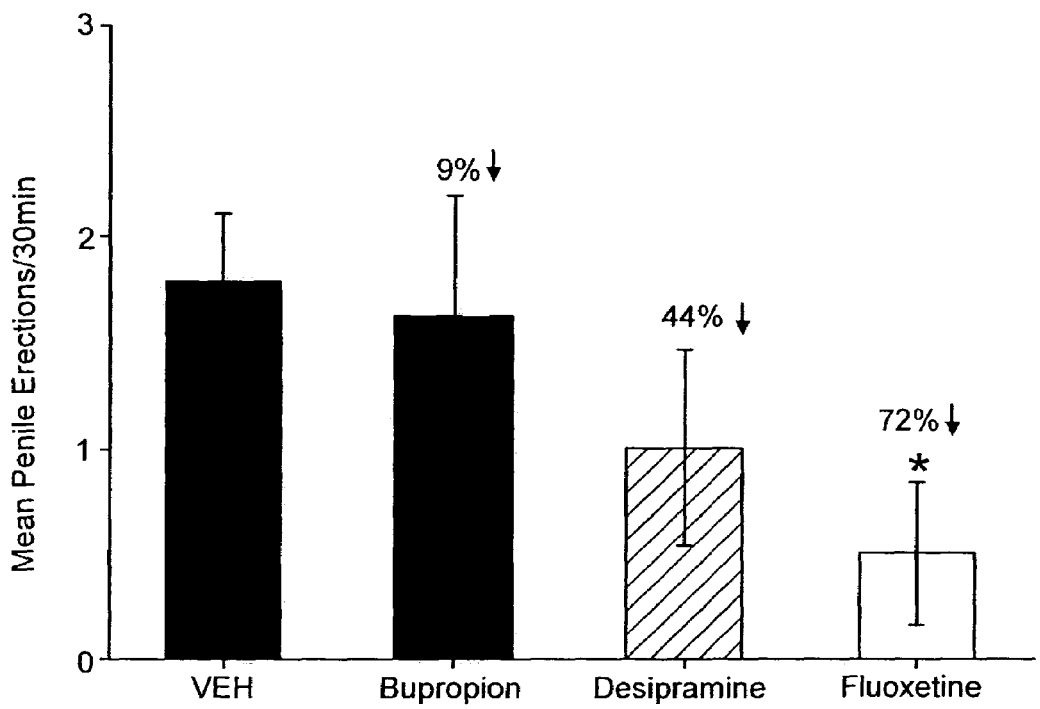
FIG. 1 is a bar graph depicting the results of experiments assaying the number of non-contact penile erections in a 30 minute test period in sexually experienced rats that were treated with intraperitoneally (i.p.) with vehicle alone (0.9% saline), bupropion (20 mg/kg ), desipramine (10 mg/kg), or fluoxetine (10 mg/kg) for 14 days.

All three compounds produced a decrease in sexual function under the experimental conditions compared to treatment with vehicle alone (FIG. 1). These data demonstrate that sexual dysfunction is induced in the animal model using drugs that are associated with sexual dysfunction in humans, thereby providing support for the validity of using the animal model.

To examine the time course of the effects of a drug that causes sexual dysfunction, rats that were handled and tested as described above were treated acutely: rats were treated with vehicle for 6 days, and on the test day (day 7) instead of vehicle, the animals received a single dose of fluoxetine in vehicle (i.p.). For a subchronic (7 day) study, fluoxetine was administered each day for 7 days and the animals were evaluated on test day 7. For the chronic 14 day study, fluoxetine was administered each day for 14 days and the animals were tested on day 14. Each fluoxetine dose was 10 mg/kg in vehicle and was delivered i.p. on each of the test days as described above.

The testing session for each section of the study was begun immediately following compound administration and the behavior observed for 30 minutes immediately following the drug administration.

Figure 2:
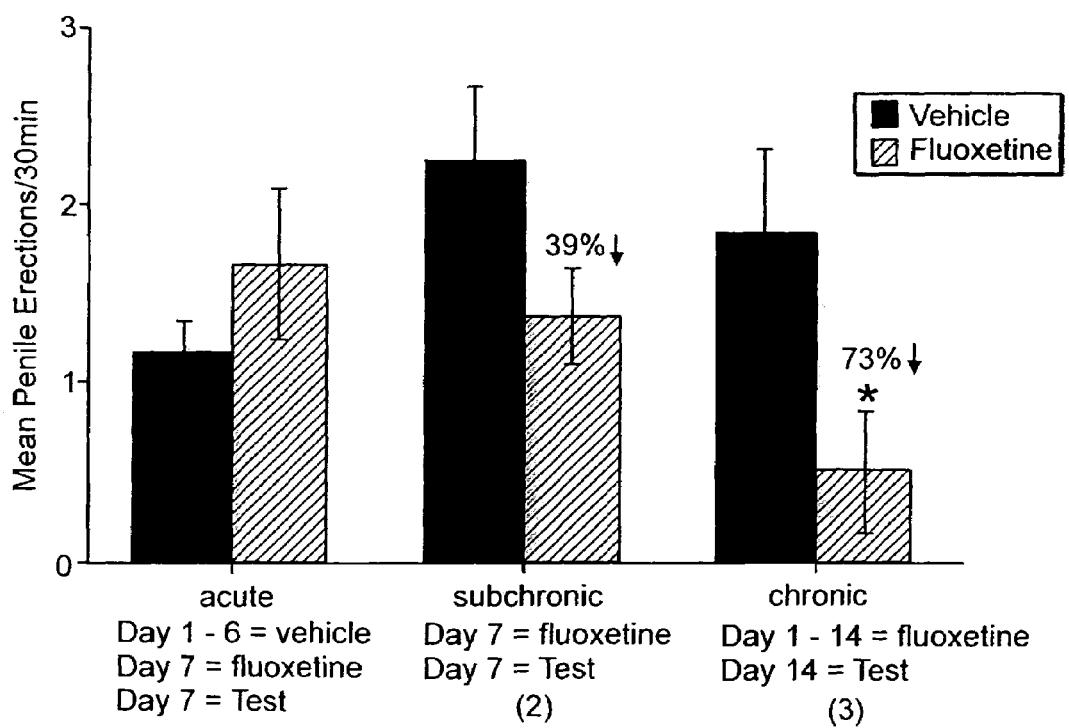
FIG. 2 is a bar graph depicting the results of experiments assaying the number of non-contact penile erections in a 30 minute test period in sexually experienced rats that were administered vehicle for 6 days and administered fluoxetine on day 7, administered fluoxetine for 7 days (subchronic); or administered fluoxetine for 14 days (chronic). Animals were tested immediately following the final administration of vehicle or drug in vehicle.

It was found that both sub-chronic and chronic administration of fluoxetine were associated with a significant increase in sexual dysfunction (FIG. 2), further demonstrating the utility of the animal model for sexual dysfunction testing.

To test the ability of a 5-HT$_{1A}$ antagonist to ameliorate the effects of sexual dysfunction, sexually experienced rats were administered an SSRI using an acute or subchronic (7 day) schedule and then tested for sexual function as described above.

Figure 3:
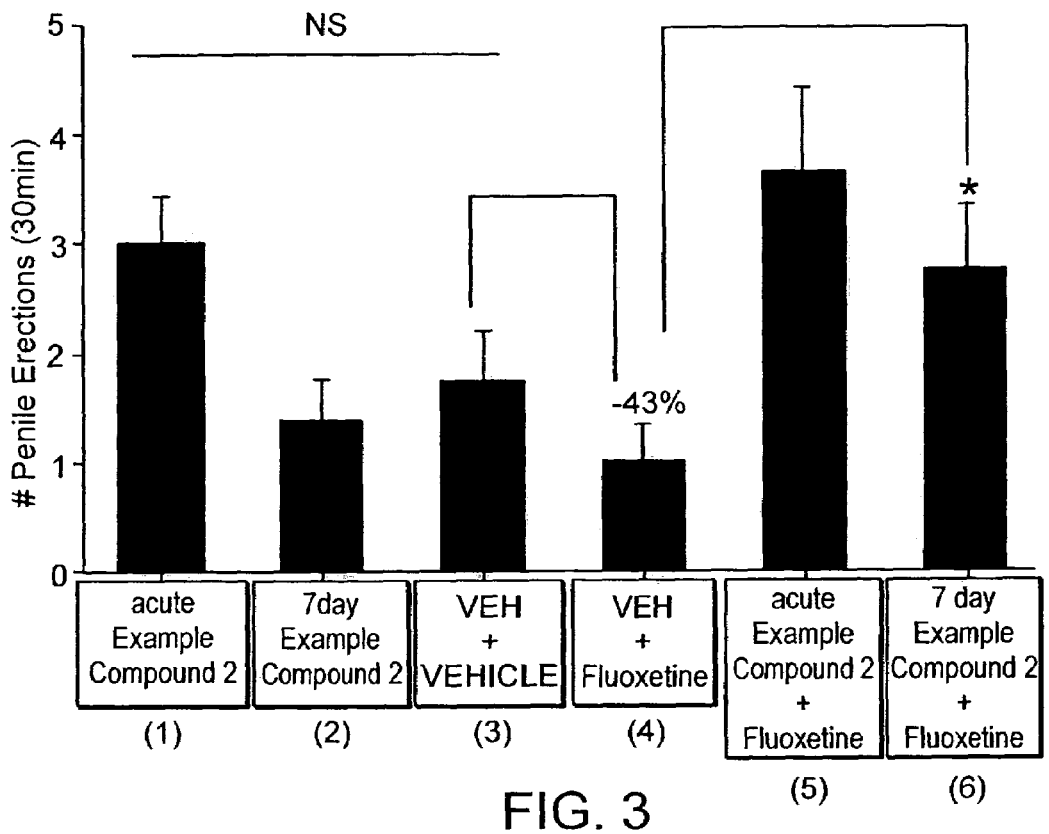
FIG. 3 is a bar graph depicting the results of experiments assaying the number of non-contact penile erections in a 30 minute test period in sexually experienced rats that were treated with vehicle (0.9% saline) only, N-[2-[4-(2-methoxyphenyl)-1-piperazinyl]ethyl-N-(2-pyridinyl)cyclohexanecarboxamide) (Example compound 2), (acutely or subchronically), fluoxetine, or Example compound 2 and fluoxetine. The treatment groups were as follows (from left to right in the Fig.): Group 1=vehicle on days 1-6, a single dose of Example compound 2 on day 7; Group 2=Example compound 2 on days 1-7; Group 3=vehicle only on days 1-7; Group 4=fluoxetine on days 1-7; Group 5=fluoxetine on days 1-6 and Example compound 2+fluoxetine on day 7; Group 6=Example compound 2+fluoxetine on days 1-7. Animals were tested immediately after the final treatment. Drugs and compounds were delivered in vehicle.

A single acute dose of a compound (Example compound 2) ameliorated sexual dysfunction when the compound was administered after a period of time in which some level of drug-induced sexual dysfunction had occurred. Thus, acute treatment of sexual dysfunction can result in an increased (e.g., normal) level of sexual functioning. This is supported by the data of those treatment groups in FIG. 3, FIG. 4, and FIG. 5, in which Example compound 2 or Example compound 3 were administered acutely after 7 or 14 days of fluoxetine treatment, and produced a complete and significant reversal of fluoxetine-induced sexual dysfunction. These data indicate that acute administration of a 5-HT$_{1A}$ antagonist with a drug that induces sexual dysfunction is useful for ameliorating the effects of the drug associated with sexual dysfunction. These data also indicate that acute treatment with a 5-HT$_{1A}$ antagonist alone improves sexual function (FIG. 3).

Figure 4:
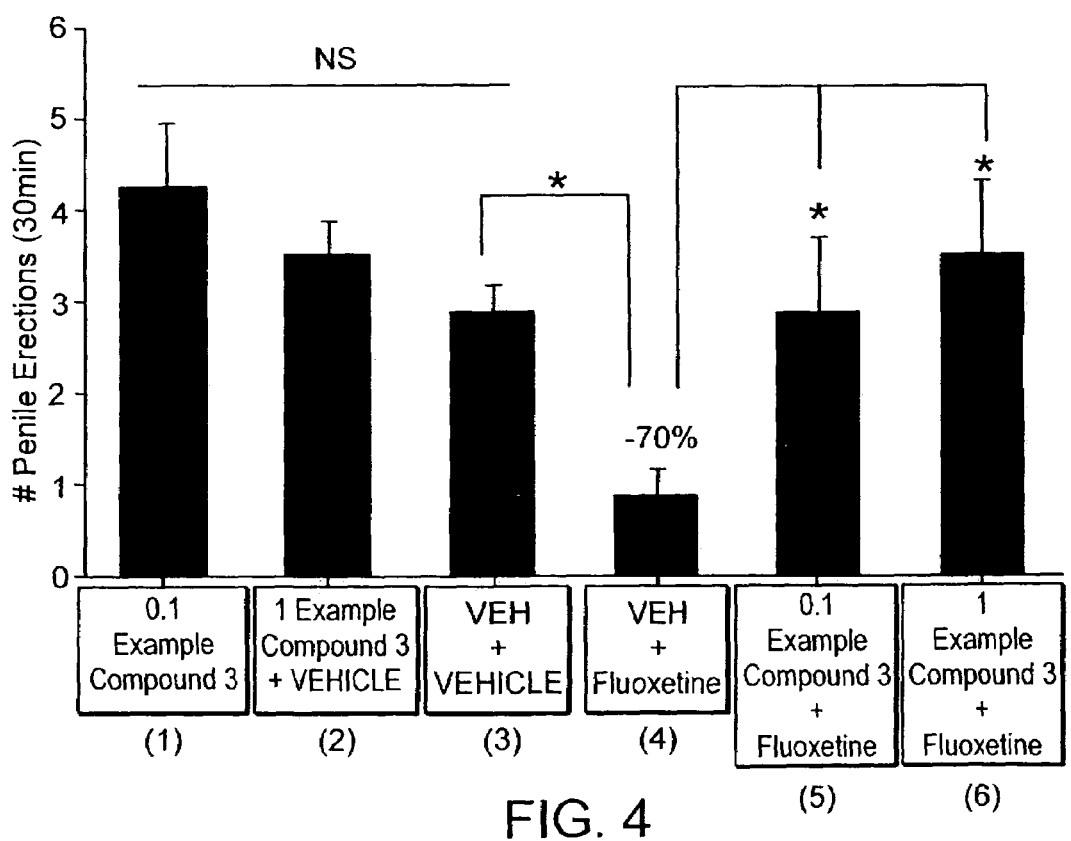
FIG. 4 is a bar graph depicting the results of experiments assaying the number of non-contact penile erections in a 30 minute test period in sexually experienced rats that were treated with the following: (from left to right in the Fig.) Group 1=vehicle only on days 1-13+a single administration of 0.1 mg/kg (R)-N-(2-methyl-(4-indolyl-1-piperazinyl) ethyl)-N-(2-pyridinyl)cyclohexanecarboxamide (Example compound 3) on day 14; Group 2=vehicle only on days 1-13+a single acute administration of 1.0 mg/kg Example compound 3 on day 14; Group 3=vehicle only on days 1-14; Group 4=fluoxetine on days 1-14; Group 5=fluoxetine only on days 1-13+single administration of 0.1 mg/kg Example compound 3+fluoxetine on day 14; Group 6=fluoxetine days 1-13+single administration of 1.0 mg/kg Example compound 3+fluoxetine on day 14. Animals were tested immediately after the final treatment on day 14. Drugs and compounds were delivered in vehicle.
Figure 5:
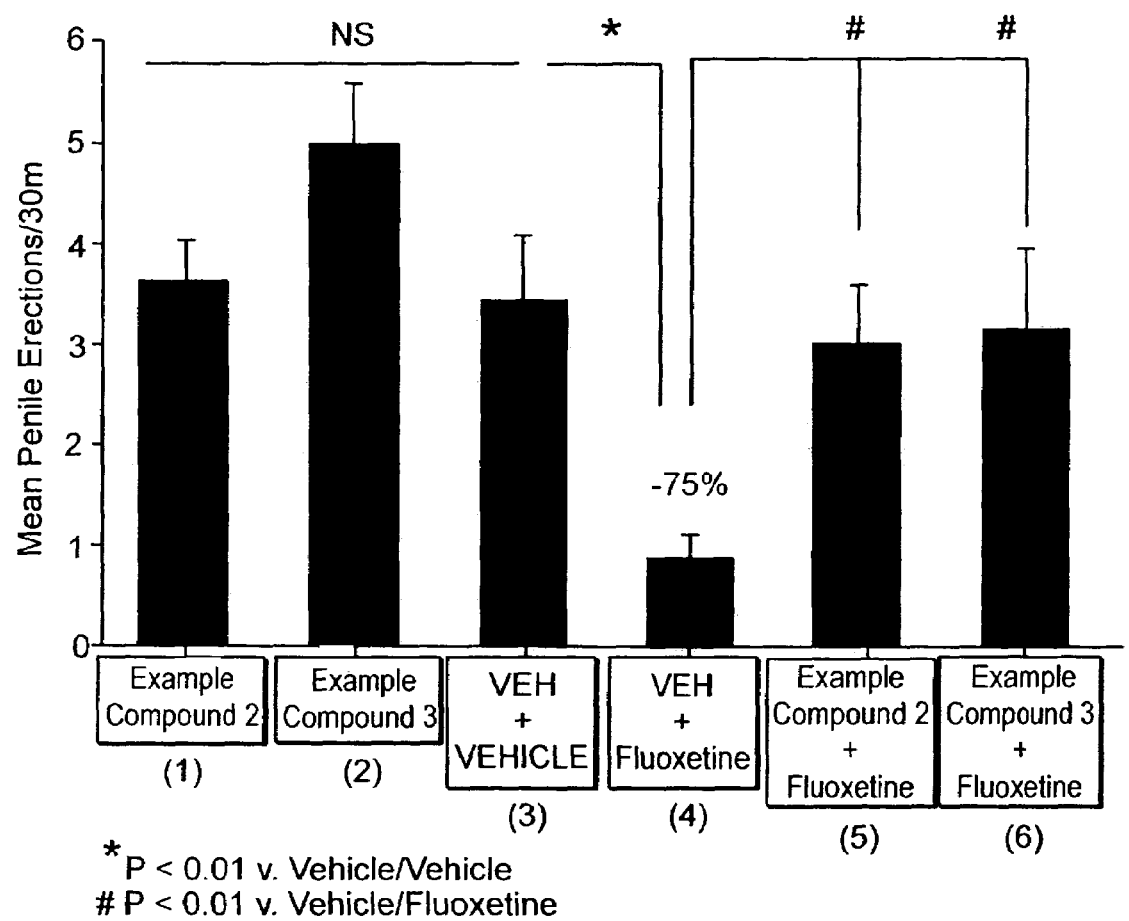
FIG. 5 is a bar graph depicting the results of experiments assaying the number of non-contact penile erections in a 30 minute test period in sexually experienced rats that were treated with the following: (from left to right in the graph): Group 1=Example compound 2 for 14 days; Group 2=Example compound 3 for 14 days; Group 3=vehicle alone for 14 days; Group 4=fluoxetine for 14 days; Group 5=Example compound 2+fluoxetine for 14 days; Group 6=Example compound 3+fluoxetine for 14 days. Animals were tested immediately after administration of the final treatment. Drugs and compounds were delivered in vehicle.

In an additional test of the ability of a 5-HT$_{1A}$ antagonist to ameliorate sexual dysfunction, Example compound 3 was administered to sexually experienced male rats using an acute schedule. In these experiments, rats were treated with vehicle only on days 1-13 then administered a single acute dose of 0.1 mg/kg of the compound (group 1), vehicle only for days 1-13 and a single dose of 1.0 mg/kg compound in vehicle on day 14 (group 2), only vehicle on days 1-14 (group 3), fluoxetine on days 1-14 (group 4), fluoxetine on days 1-13 and a single administration of 0.1 mg/kg of the compound and fluoxetine on day 14 (group 5); and fluoxetine on days 1-13 and a single dose of 1.0 mg/kg compound with fluoxetine on day 14 (group 6). For each group, behavior testing was performed for 30 minutes immediately following drug administration on day 14 only. In these experiments, two different doses of the compound were administered, 0.1 mg/kg or 1.0 mg/kg, and either dosage resulted in a full reversal of the deficits in the number of non-contact penile erections, produced by chronic (14 day) treatment with an SSRI, fluoxetine (10 mg/kg/day, i.p.). These data further indicate the efficacy of using a compound of the invention to treat sexual dysfunction, and also provide examples of effective dosages and an example of a dosage range (FIG. 4, FIG. 5).

Experiments were conducted to assess the ability of a 5-HT$_{1A}$ antagonist to prevent the effects of SSRI treatment. Rats, as described supra, were co-administered a 5-HT$_{1A}$ antagonist and an SSRI. The 5-HT$_{1A}$ antagonist was either Example compound 3 (1 mg/kg) or Example compound 2 (0.3 mg/kg). The administered SSRI was fluoxetine (10 mg/kg). The 5-HT$_{1A}$ antagonist and SSRI were co-administered for 7 or 14 days with the SSRI. Under these conditions, 5-HT$_{1A}$ antagonist prevented the deficit in non-contact penile erections produced by chronic fluoxetine treatment alone. These data demonstrate that chronic treatment with a 5-HT$_{1A}$ antagonist, when co-administered with an SSRI, can prevent or ameliorate sexual dysfunction associated with SSRI treatment (FIG. 5, FIG. 6)

Taken together these data demonstrate the efficacy of a 5-HT$_{1A}$ antagonist for treating sexual dysfunction, e.g., that is associated with antidepressant treatment, whether treatment with the 5-HT$_{1A}$ antagonist is initiated at the same time as antidepressant treatment (e.g., SSRI treatment) or when treatment with the 5-HT$_{1A}$ is provided after initiation of treatment with the antidepressant.

The effects of 14 day chronic treatment of the animal model is tested in an animal provided with a 5-HT$_{1A}$ antagonist that is administered orally (p.o.) or i.p., or fluoxetine (i.p.). The effect of the two treatments on penile erections in sexually experienced male rats is tested. The ability of the compounds to affect the number of non-contact penile erections relative to vehicle treated animals is determined and the results between the two treatment regimes are compared. It is expected that a compound useful for treating SSRI-related sexual dysfunction is will exhibit minimal or no effects on sexual function as determined by the assay relative to SSRI-treated animals.

The Examples provided supra illustrate methods that can be used to test compounds described herein for their ability to ameliorate sexual dysfunction associated with drug treatment. Other models known in the art for testing sexual dysfunction associated with antidepressant, antipsychotic, or anticonvulsant treatment can be used.

Other Embodiments

The present invention may be embodied in other specific forms without departing from the spirit and essential attributes thereof and, accordingly, reference should be made to the appended claims, rather than to the foregoing specification, as indicating the scope of the invention.

What is claimed is:

1. A method for treating urinary incontinence in a patient in need thereof, comprising administering to the patient an effective amount of a compound of formula (III):

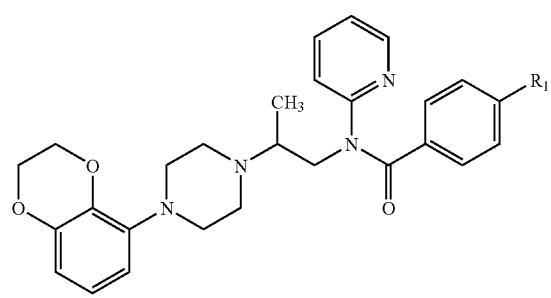

(III)

wherein R$_1$ is cyano, nitro, trifluoromethyl or halogen, or pharmaceutically acceptable acid addition salts thereof.

* * * * *